United States Patent
Yamamura

(10) Patent No.: US 12,284,454 B2
(45) Date of Patent: Apr. 22, 2025

(54) IMAGING SYSTEM, CONTROL UNIT, CAMERA UNIT, ENDOSCOPIC SCOPE, AND ENDOSCOPIC SYSTEM

(71) Applicant: OLYMPUS MEDICAL SYSTEMS CORP., Hachioji (JP)

(72) Inventor: Daiki Yamamura, Machida (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 71 days.

(21) Appl. No.: 18/368,125

(22) Filed: Sep. 14, 2023

(65) Prior Publication Data

US 2024/0007766 A1    Jan. 4, 2024

Related U.S. Application Data

(63) Continuation of application No. PCT/JP2021/010315, filed on Mar. 15, 2021.

(51) Int. Cl.
*H04N 25/709* (2023.01)
*H04N 7/10* (2006.01)
*H04N 23/50* (2023.01)

(52) U.S. Cl.
CPC .......... *H04N 25/709* (2023.01); *H04N 7/10* (2013.01); *H04N 23/555* (2023.01)

(58) Field of Classification Search
CPC ...... H04N 25/709; H04N 7/10; H04N 23/555; H04N 23/65; A61B 1/00; A61B 1/05; G03B 17/02
See application file for complete search history.

(56) References Cited

U.S. PATENT DOCUMENTS

| | | | | |
|---|---|---|---|---|
| 7,365,768 B1* | 4/2008 | Ono | | H04N 23/661 |
| | | | | 600/101 |
| 2016/0331211 A1* | 11/2016 | Fujisawa | | A61B 1/009 |
| 2019/0089920 A1* | 3/2019 | Nakamura | | H04N 25/709 |

(Continued)

FOREIGN PATENT DOCUMENTS

| | | |
|---|---|---|
| JP | 1-110568 U | 7/1989 |
| JP | 7-283981 A | 10/1995 |
| JP | 2011-206333 A | 10/2011 |

(Continued)

OTHER PUBLICATIONS

International Search Report dated Jun. 8, 2021, issued in counterpart International Application No. PCT/JP2021/010315, with English Translation. (5 pages).

*Primary Examiner* — Timothy J Henn
(74) *Attorney, Agent, or Firm* — WHDA, LLP

(57) ABSTRACT

An imaging system according to the present disclosure has a camera unit and a control unit that are connected via a transmission cable having a power signal line and a video signal line. The camera unit includes an imaging element and a selector circuit. The control unit includes a supply voltage control circuit, a feedback value measurement circuit, and an arithmetic circuit that calculates a resistance value R3 related to a resistance value R1 of the video signal line and a resistance value R2 of the power signal line from the supply voltage Vctrl, the feedback voltage Vfb and the feedback current Ifb, and calculates a drive voltage Vcis based on the resistance value R2, the supply current Ictrl, and the supply voltage Vctrl.

10 Claims, 8 Drawing Sheets

(56) References Cited

U.S. PATENT DOCUMENTS

2020/0237183 A1\* 7/2020 Yanagisawa ....... A61B 1/00057

FOREIGN PATENT DOCUMENTS

| JP | 2014-36724 A | 2/2014 | |
|---|---|---|---|
| JP | 2015-192695 A | 11/2015 | |
| JP | 2016-214571 A | 12/2016 | |
| WO | WO-2019123715 A1 \* | 6/2019 | ............... A61B 1/00 |

\* cited by examiner

IMAGING SYSTEM, CONTROL UNIT, CAMERA UNIT, ENDOSCOPIC SCOPE, AND ENDOSCOPIC SYSTEM

CROSS-REFERENCE TO RELATED APPLICATIONS

The present application is a continuation application based on PCT Patent Application No. PCT/JP2021/010315, filed on Mar. 15, 2021, the entire content of which is hereby incorporated by reference.

BACKGROUND

Technical Field

The present disclosure relates to an imaging system, a control unit, a camera unit, an endoscopic scope, and an endoscopic system.

Description of the Background

The endoscopic system includes a camera unit having an imaging device and a control unit. The camera unit and control unit are connected by a transmission cable having a power signal line and a video signal line. Power for driving the camera unit and control signals for controlling the camera unit are transmitted from the control unit via transmission cables.

In order to drive the image sensor, the control unit supplies power to the image sensor via the power signal line. Assuming that the value of the current flowing through the power signal line is I, a voltage Vcis for driving the imaging device is a value that is RI lower than a voltage Vout supplied by the control unit due to an electrical resistance R of the power signal line. Therefore, the voltage Vout supplied by the control unit needs to be increased in consideration of the voltage drop RI in the power signal line.

When the voltage Vout supplied by the control unit is increased, the power consumption of the imaging device and the amount of heat generated by the power signal line may increase, which may adversely affect body tissues. Also, the current value I flowing through the power signal line changes depending on the driving state of the imaging device. Therefore, it is required to monitor the voltage Vcis for driving the imaging device and adjust the voltage Vcis to a desired voltage, far example, 3.3 V which is the recommended operating voltage.

As a technique for adjusting the voltage Vcis that drives the imaging device, for example, Japanese Unexamined Patent Application, First Publication No. 2011-206333 (hereinafter referred to as Patent Document 1) discloses a technique of connecting the distal end of the endoscopic scope and a control unit with a feedback cable and measuring the voltage at the distal end of the endoscopic scope with the feedback cable.

Installing a dedicated line for measuring voltage hinders the thinning of the transmission cable.

SUMMARY

The present disclosure provides an imaging system, a control unit, a camera unit, an endoscopic scope, and an endoscopic system that can monitor the voltage supplied to the imaging device and can realize a thin transmission cable.

A first aspect of the present disclosure is an imaging system in which a camera unit and a control unit are connected by a transmission cable having a power signal line and a video signal line, wherein the camera unit includes an imaging device that is driven by a drive voltage Vcis and generates a photoelectric conversion signal according to the amount of light received, and a selector circuit that switches a current flow path so that a resistance value R2 of the power signal line can be calculated, and the control unit includes a supply voltage control circuit that controls a supply voltage Vctrl, a feedback value measurement circuit that measures a feedback voltage Vfb that is a voltage on the control unit side of the video signal line, a feedback current Iib that is a current on the control unit side after passing through the video signal line, and a supply current Ictrl corresponding to the supply voltage Vctrl, and an arithmetic circuit that calculates a resistance value R3 related to a resistance value R1 of the video signal line and a resistance value R2 of the power signal line from the supply voltage Vctrl, the feedback voltage Vfb and the feedback current Ifb, and calculates a drive voltage Vcis based on the resistance value R2, the supply current Ictrl, and the supply voltage Vctrl.

A second aspect of the present disclosure is a control unit control unit that is connectable to a camera unit equipped with an imaging device via a power signal line and a video signal line, including: a supply voltage control circuit that controls the supply voltage Vctrl; a feedback value measurement circuit that measures a feedback voltage Vfb that is a voltage on the control unit side of the video signal line, a feedback current Ifb that is a current on the control unit side after passing through the video signal line, and a supply current Ictrl corresponding to the supply voltage Vctrl; and an arithmetic circuit that calculates a resistance value R3 related to a resistance value R1 of the video signal line and a resistance value R2 of the power signal line from the supply voltage Vctrl, the feedback voltage Vfb, and the feedback current Ifb, and calculates a drive voltage Vcis from the resistance value R2, the supply current Ictrl, and the supply voltage Vctrl.

A third aspect of the present disclosure is an endoscopic system including the above imaging system.

According to the imaging system, the control unit, the camera unit, the endoscopic scope, and the endoscopic system of the present disclosure, it is possible to monitor the voltage supplied to the imaging device and to achieve a thinner transmission cable.

EMBODIMENTS

Figure 1:
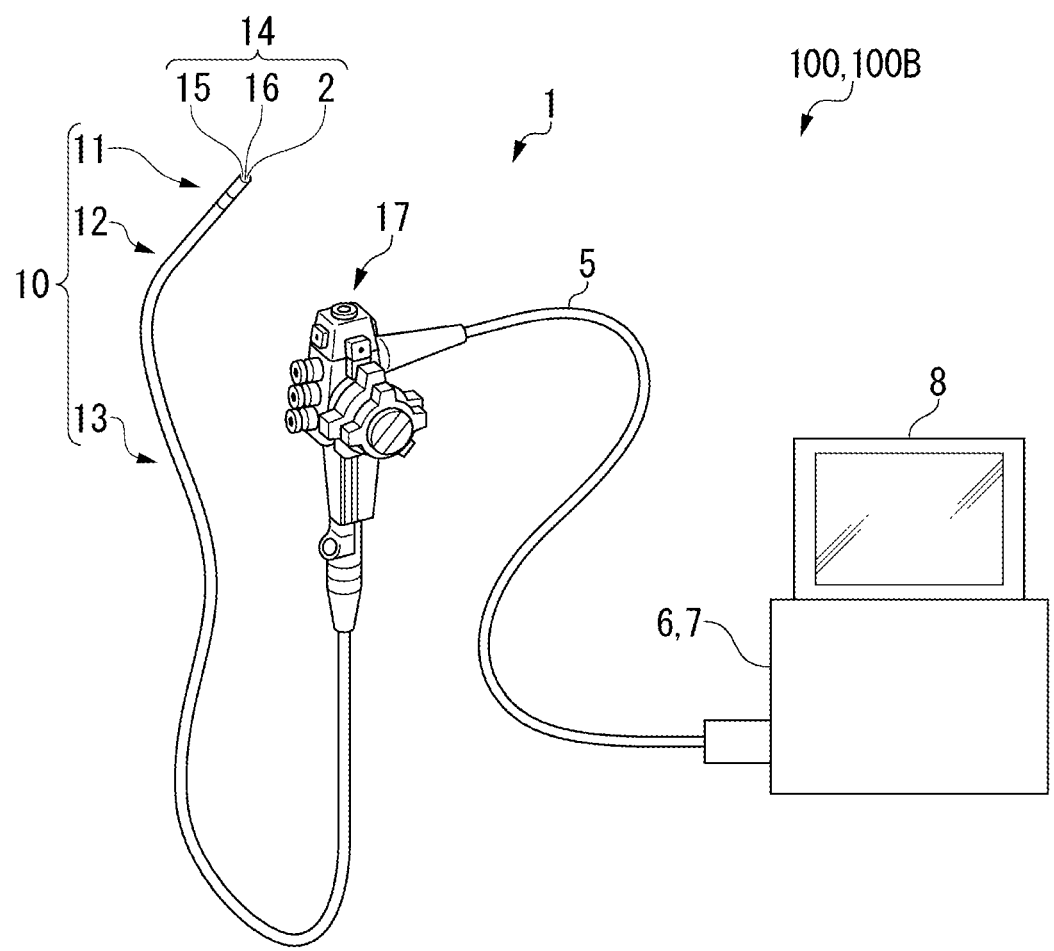
FIG. 1 is a perspective view showing an endoscopic system according to a first embodiment of the present disclosure.

Hereinafter, embodiments of the present disclosure will be described in detail with reference to the drawings. An imaging system according to the present disclosure includes an endoscopic system. Therefore, it can be said that the endoscopic system described below is an embodiment of the imaging system according to the present disclosure.

First Embodiment

An endoscopic system 100 according to a first embodiment of the present disclosure will be described with reference to FIGS. 1 to 5. It should be noted that the dimensions and ratios of each component in the drawing do not represent the actual dimensions and ratio of each component.

[Endoscopic System 100]

FIG. 1 is a perspective view of the endoscopic system 100. The endoscopic system 100 includes an endoscope 1, a universal cord 5, a control unit 6, a light source device 7, and a display device 8. The control unit 6 and the light source device 7 are connected to the endoscope 1 via the universal cord 5.

The endoscope 1 is a device for observing or treating a diseased part inside the body. The endoscope 1 includes an insertion portion 10 and an operation portion 17. In this embodiment, the endoscope 1 is a flexible endoscope, but the endoscope 1 may be another type of endoscope (for example, a rigid endoscope or an ultrasonic endoscope).

The insertion portion 10 is a long tubular member that is inserted into the body. The insertion portion 10 has a hard distal end portion 11, a bending portion 12 that can bend in a plurality of different directions, and a flexible tube portion 13 that has flexibility. The distal end portion 11, the bending portion 12, and the flexible tube portion 13 are connected in order from the distal end side. The flexible tube portion 13 is connected to the operation portion 17.

The distal end portion 11 has an endoscopic scope 14. The endoscopic scope 14 has a light source 15, an optical system 16, and a camera unit 2. The bending portion 12 bends as the operator operates the operation portion 17. The flexible tube portion 13 is a tubular portion having flexibility.

The operation portion 17 accepts operations for the endoscope 1. The universal cord 5 is connected to the operation portion 17.

The control unit 6 comprehensively controls the entire endoscopic system 100. The control unit 6 applies image processing to the video signal output from the camera unit 2.

The light source device 7 supplies illumination light emitted by the light source 15. The light source device 7 has, for example, a halogen lamp or an LED. The light source device 7 supplies the generated illumination light to the light source 15 under the control of the control unit 6.

The display device 8 displays an image of the affected area captured by the endoscope 1, various information about the endoscopic system 100, and the like.

Figure 2:
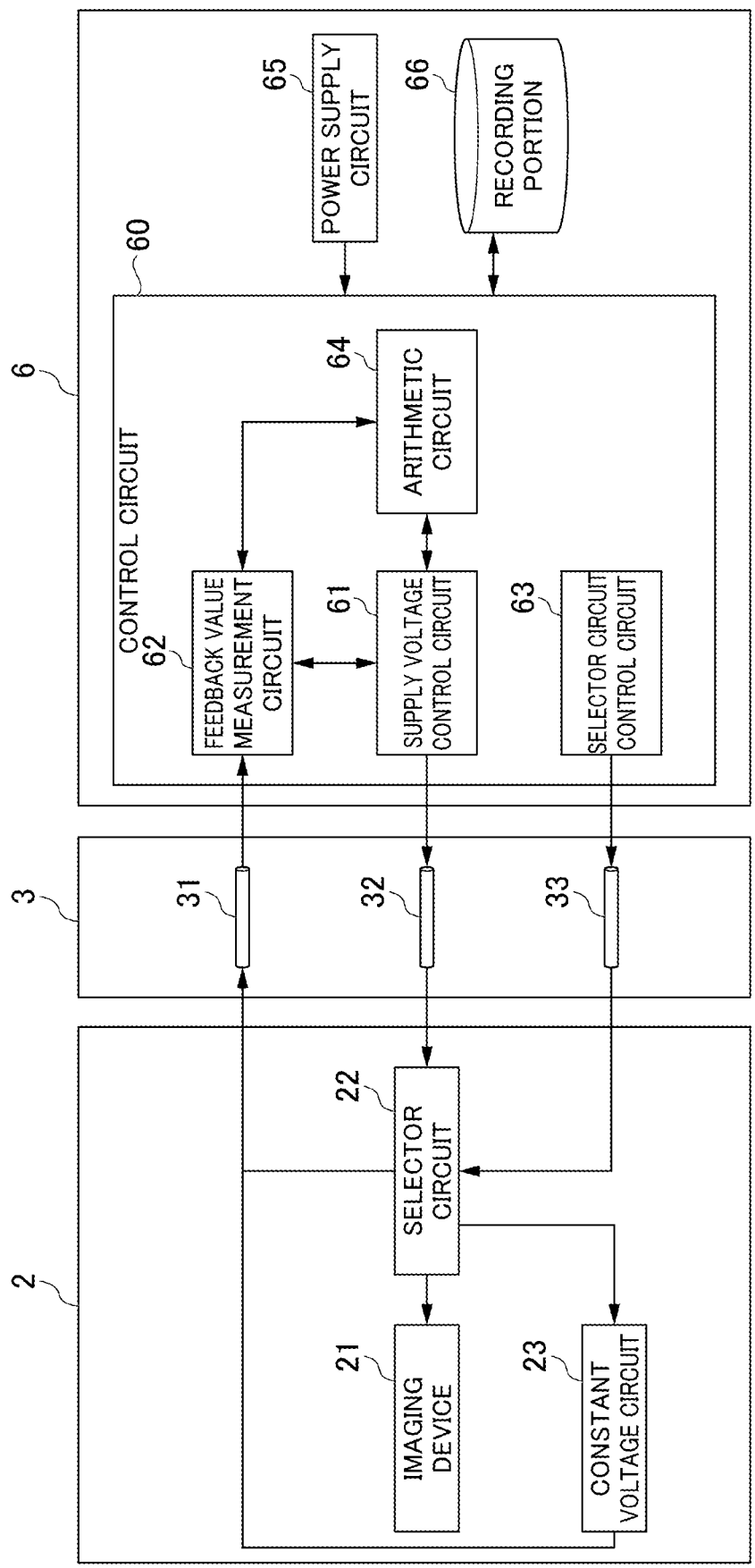
FIG. 2 is a block diagram of a camera unit and a control unit included in the endoscopic system according to the embodiment.

FIG. 2 is a block diagram of the camera unit 2 and control unit 6 provided in the endoscopic system 100 according to this embodiment.

The camera unit 2 and the control unit 6 are connected by a transmission cable 3. The transmission cable 3 is a general term for a transmission path composed of a cable inserted through the insertion portion 10 of the endoscope 1, the universal cord 5, and the like. The transmission cable 3 has a video signal line 31 for transmitting video signals, a power signal line 32 for transmitting power, and a control signal line 33 for transmitting signals for controlling the camera unit 2. The control signal line 33 transmits signals and clock signals for controlling a selector circuit 22, which will be described later.

[Camera Unit (Imaging Device) 2]

The camera unit (imaging device) 2 converts the subject image formed via the optical system 16 to generate an imaging signal. The camera unit 2 outputs the generated imaging signal to the control unit 6 via the video signal line 31. The camera unit 2 also receives power supply from the control unit 6 via the power signal line 32.

The camera unit 2 has an imaging device 21, the selector circuit 22, and a constant voltage circuit 23, as shown in FIG. 2.

The imaging device 21 is specifically an image sensor, such as a CCD image sensor or a CMOS image sensor. The imaging device 21 is driven by a drive voltage Vcis, receives the subject image formed by the optical system 16, and generates a photoelectric conversion signal corresponding to the amount of received light. The drive voltage Vcis is a voltage supplied to the imaging device 21, and refers to a voltage between a voltage pad of the imaging device 21 and a power supply voltage supply point of the imaging device 21.

The selector circuit 22 switches the path through which the current flows so that the resistance value R2 of the power signal line 32 can be calculated. Specifically, the selector circuit 22 switches a plurality of paths through which current flows among the camera unit 2, the transmission cable 3, and the control unit 6. The plurality of paths will be described in [Operation of Endoscopic system 100].

The constant voltage circuit 23 is a circuit that supplies a predetermined voltage V1 to the video signal line 31. The constant voltage circuit 23 is, for example, a known three-terminal regulator, and has an input terminal, an output terminal, and a common terminal. The input terminal is connected to the selector circuit 22, the output terminal is connected to the video signal line 31, and the common terminal is grounded.

[Control Unit (Control Device) 6]

The control unit (control device) 6 has a control circuit 60, a power supply circuit 65, and a recording portion 66, as shown in FIG. 2.

The control circuit 60 centrally controls the entire endoscopic system 100. The control circuit 60 applies image processing to the video signal output from the camera unit 2. The control circuit 60 transfers an image to be displayed on the display device 8.

The control circuit 60 is a program-executable processing circuit (computer) having one or more processors (CPU, GPU, DSP, etc.) and a program-readable memory. The control circuit 60 controls the endoscopic system 100 by executing an endoscope control program. The control circuit 60 may include a dedicated circuit. The dedicated circuit is a processor separate from the processor included in the control circuit 60, a logic circuit implemented in an ASIC or FPGA, or a combination thereof.

The control circuit 60 has a supply voltage control circuit 61, a feedback value measurement circuit 62, a selector circuit control circuit 63, and an arithmetic circuit 64.

The supply voltage control circuit 61 controls the supply voltage Vctrl, which is the voltage supplied to the camera unit 2. The supply voltage control circuit 61 changes the supply voltage Vctrl based on the feedback voltage Vfb and the feedback current Ifb measured by the feedback value measurement circuit 62, for example.

The feedback value measurement circuit 62 measures the feedback voltage Vfb on the control unit 6 side of the video signal line 31, the feedback current Ifb which is the current on the control unit 6 side after passing through the video signal line 31, and the supply current Ictrl corresponding to the supply voltage Vctrl.

The selector circuit control circuit 63 transmits a control signal for controlling the selector circuit 22 via the control signal line 33.

The arithmetic circuit 64 calculates the resistance value R3 (the sum R1+R2 of the resistance value R1 of the video signal line 31 and the resistance value R2 of the power signal line 32 based on the following equation (1) from the supply voltage Vctrl, the feedback voltage Vfb, and the feedback current Ifb). Further, the arithmetic circuit 64 calculates the drive voltage Vcis from the resistance value R2, the supply current Ictrl, and the supply voltage Vctrl based on the following equation (2).

$$R1+R2=(Vctrl-Vfb)/Ifb \qquad \text{Equation (1)}$$

$$Vctrl=Vcis+R2 \times Ictrl \qquad \text{Equation (2)}$$

The arithmetic circuit 64 may calculate the resistance value R1 of the video signal line 31 from the following equation (3) based on the predetermined voltage V1 supplied by the constant voltage circuit 23.

$$R1=(V1-Vfb)/Ifb \qquad \text{Equation (3)}$$

The power supply circuit 65 supplies power for driving the control circuit 60, the recording portion 66, and the camera unit 2. Power for driving the camera unit 2 is controlled by the supply voltage control circuit 61 and supplied via the power signal line 32.

The recording unit 66 is a non-volatile recording medium that stores each program executed by each component described above and data necessary for executing each program. The recording unit 66 includes, for example, a flexible disk, a magneto-optical disk, a ROM, a writable nonvolatile memory such as a flash memory, a portable medium such as a CD-ROM, a storage device such as a hard disk built into a computer system, and the like.

[Operation of the Endoscopic System 100]

Figure 3:
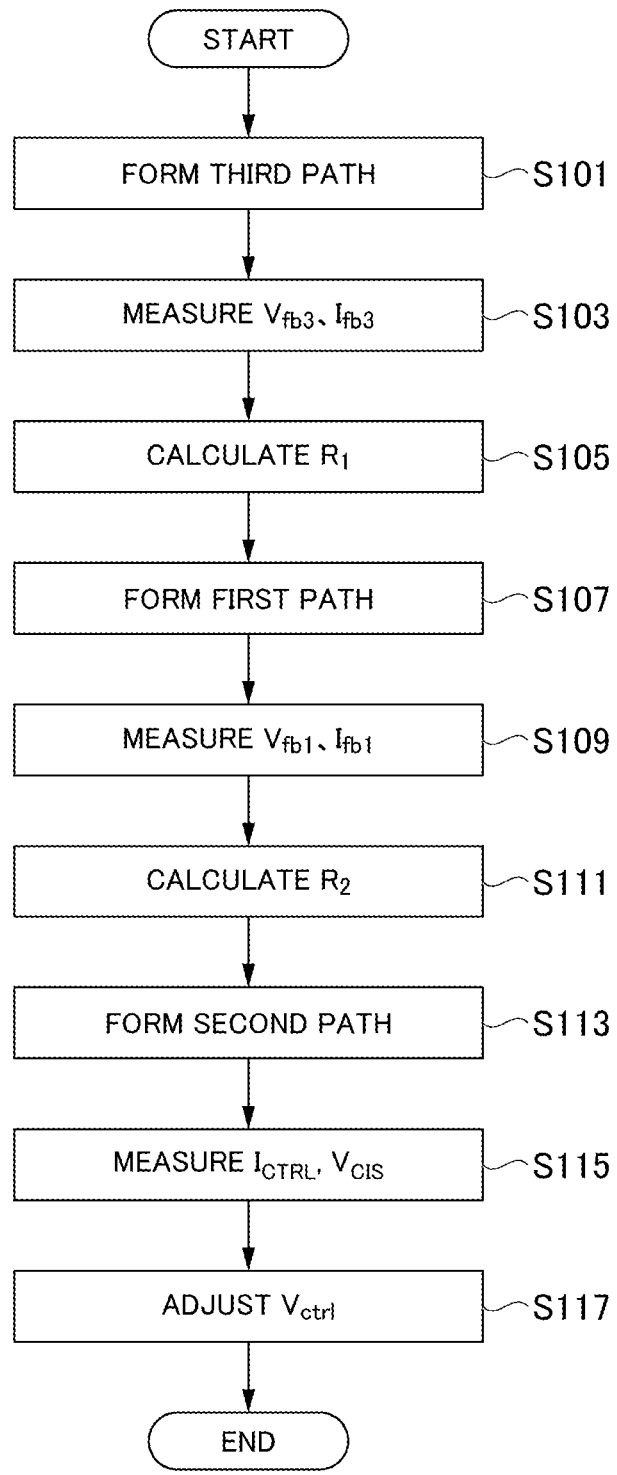
FIG. 3 is a flowchart showing an overview of operation processing executed by the endoscopic system according to the embodiment.
Figure 4:
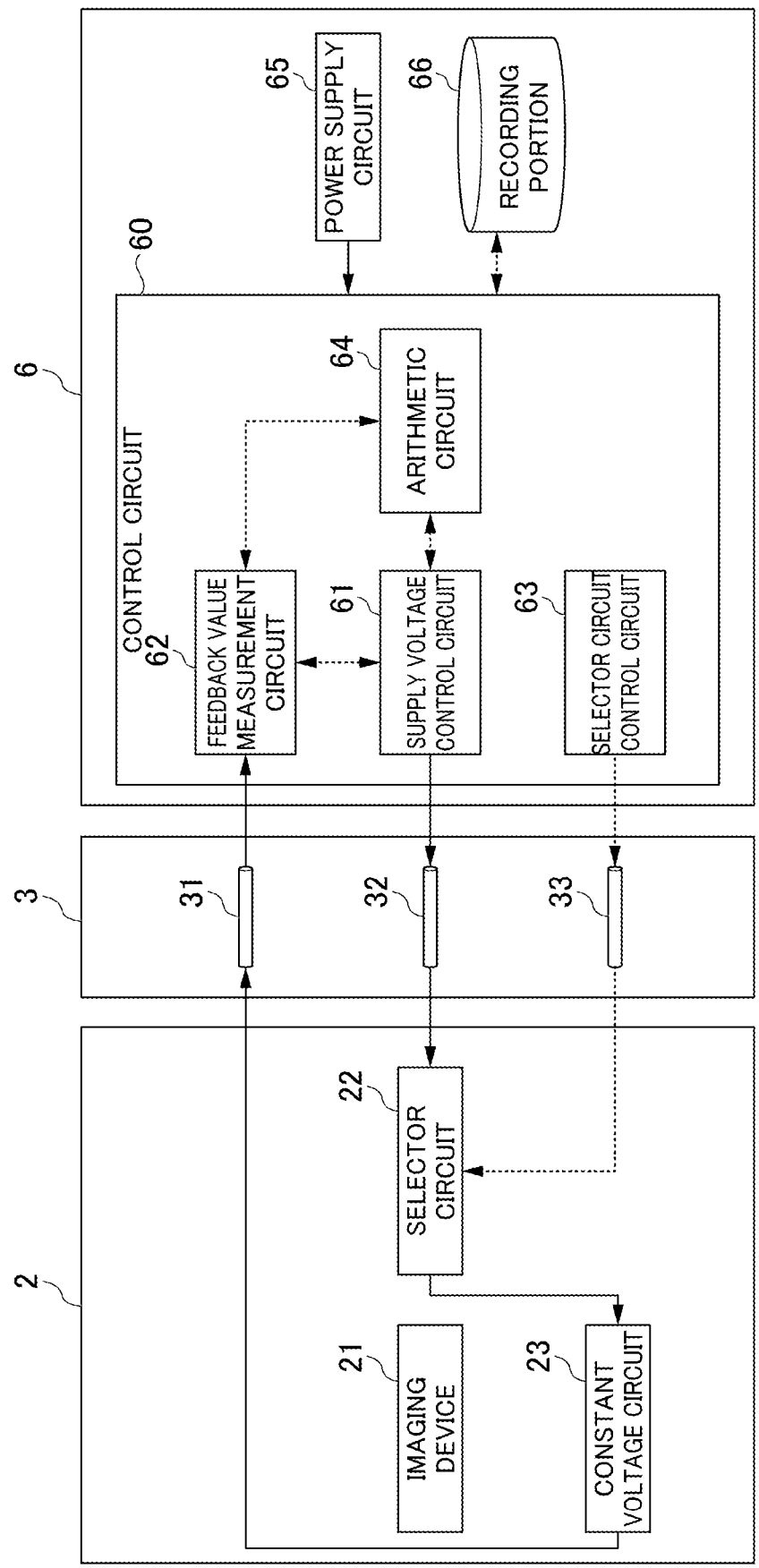
FIG. 4 is a block diagram showing a third route in the endoscopic system according to the embodiment.
Figure 5:
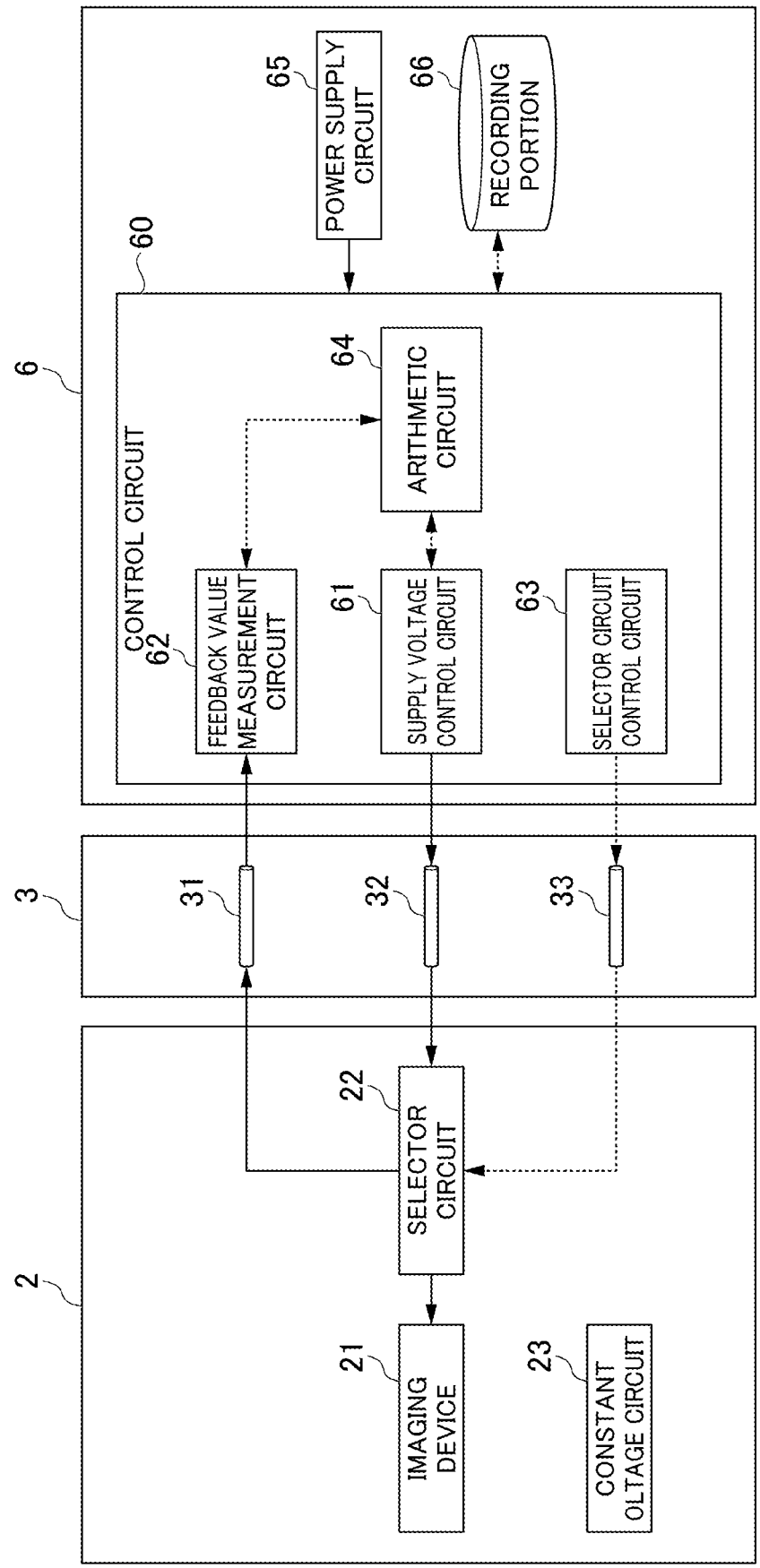
FIG. 5 is a block diagram showing a first route in the endoscopic system according to the embodiment.
Figure 6:
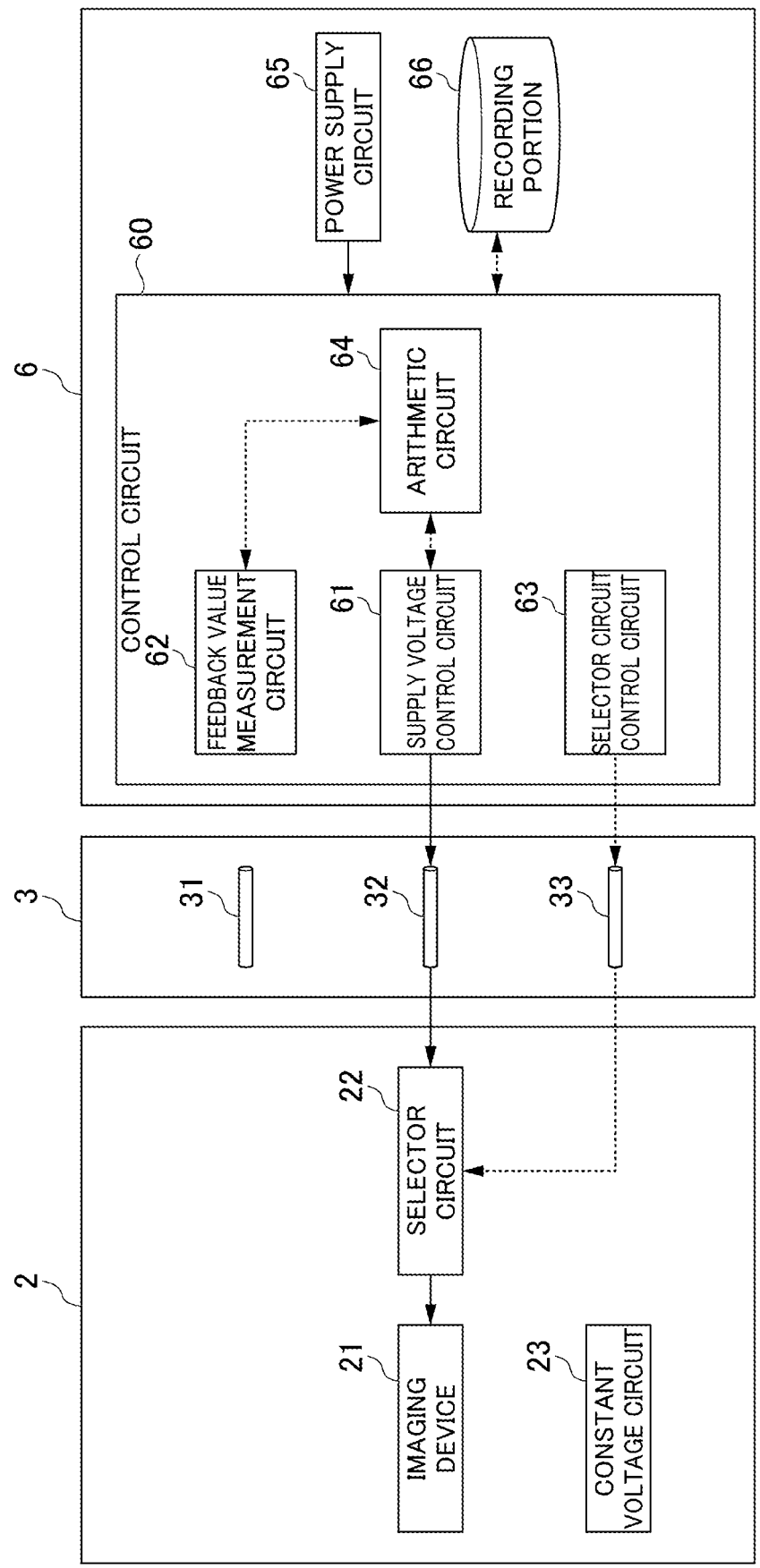
FIG. 6 is a block diagram showing a second route in the endoscopic system according to the embodiment.

Next, the operation of the endoscopic system 100 (control method of the endoscopic system 100) will be described with reference to FIGS. 3 to 6. FIG. 3 is a flowchart showing an outline of operation processing executed by the endoscopic system 100. FIG. 4 is a block diagram showing the third route in the endoscopic system 100 according to this embodiment. FIG. 5 is a block diagram showing the first route in the endoscopic system 100 according to this embodiment. FIG. 6 is a block diagram showing the second route in the endoscopic system 100 according to this embodiment. In FIGS. 4 to 6, solid lines indicate power lines to which power is supplied, and dashed lines indicate control lines. In the following, for convenience, the feedback voltage in the second path is sometimes referred to as a feedback voltage Vfb2, the feedback current in the first path is sometimes referred to as a feedback current Ilb1, the feedback voltage in the third path is sometimes referred to as a feedback voltage Vlb1, and the feedback current in the third path is sometimes referred to as a feedback current Ifb3.

First, in the blanking period, as shown in FIG. 4, the selector circuit control circuit 63 transmits a control signal to the selector circuit 22 via the control signal line 33, and the selector circuit 22 forms a third path to which the supply voltage control circuit 61, the power signal line 32, the constant voltage circuit 23, the video signal line 31, and the feedback value measurement circuit 62 are connected (step S101). After the third path is formed, the voltage supplied from the power supply circuit 65 to the control unit 6 is controlled by the supply voltage control circuit 61 and supplied to the constant voltage circuit 23 via the power signal line 32 and the selector circuit 22. The constant voltage circuit 23 converts the supplied voltage into a predetermined voltage V1 and supplies it to the video signal line 31, and the feedback value measurement circuit 62 measures a feedback voltage Vfb3 and the feedback current Ifb3 in the third path based on the voltage V1 (step S103). The arithmetic circuit 64 calculates the resistance value R1 of the video signal line 31 from the following equation (4) (step S105).

$$R1=(V1-Vfb3)/Ifb3 \qquad \text{Equation (4)}$$

Next, as shown in FIG. 5, the selector circuit control circuit 63 transmits a control signal to the selector circuit 22 via the control signal line 33, and the selector circuit 22 forms a first path to which the supply voltage control circuit 61, the power signal line 32, the video signal line 31 and the feedback value measurement circuit 62 are connected (step S107). The supply voltage control circuit 61 supplies the supply voltage Vctrl and the supply current Ictrl to the power signal line 32, and the feedback value measurement circuit 62 measures the feedback voltage Vfb1 and the feedback current Ifb1 in the first path based on the supply voltage Vctrl (step S109). The arithmetic circuit 64 calculates the sum R1+R2 of the resistance value R1 of the video signal line 31 and the resistance value R2 of the power signal line 32 from the following equation (2) (step S111). Since the resistance value R1 of the video signal line 31 is calculated in step S105, the resistance value R2 of the power signal line 32 is calculated in step S111.

$$R1+R2=(Vctrl-Vfb1)/Ifb1 \qquad \text{Expression (5)}$$

Next, as shown in FIG. 6, the selector circuit control circuit 63 transmits a control signal to the selector circuit 22 via the control signal line 33, and the selector circuit 22 forms a second path to which the supply voltage control circuit 61, the power signal line 32, and the imaging device 21 are connected (step S113). The supply voltage control circuit 61 supplies the supply voltage Vctrl to the power signal line 32, the feedback value measurement circuit 62 measures the supply current Ictrl based on the supply voltage Vctrl, and the arithmetic circuit 64 calculates the drive voltage Vcis to be supplied to the image sensor from the following equation (6) (step S115).

$$Vctrl=Vcis+(R1 \times Ictrl) \qquad \text{Expression (6)}$$

Subsequently, the supply voltages Vctrl and Ictrl are adjusted so that the calculated drive voltage Vcis becomes a target voltage Vtarget (step S117). The target voltage Vtarget is, for example, 3.3V.

According to the endoscopic system 100 according to the present embodiment, the resistance value R1 of the video signal line 31 and the resistance value R2 of the power signal line 32 can be calculated by switching the path with the selector circuit 22. Then, the drive voltage Vcis can be monitored based on the resistance value R1 of the video signal line 31 and the resistance value R2 of the power signal line 32. Therefore, it is not necessary to provide a dedicated line for calculating the drive voltage Vcis. According to the endoscopic system 100 of the present embodiment, it is possible to reduce the diameter of the transmission cable 3 because it is not necessary to provide the dedicated line. Then, the actual drive voltage Vcis can be adjusted to the target voltage Vtarget based on the calculated drive voltage Vcis.

The first embodiment of the present disclosure has been described above in detail with reference to the drawings, but the specific configuration is not limited to this embodiment, and design changes etc. are included within the scope of the present invention. Also, the constituent elements shown in the above-described embodiment and modification can be combined as appropriate.

(Modification 1-1)

In the above embodiment, steps S101 to Sill are performed in blanking periods, but they may be performed in each blanking period, or may be performed during any one of a plurality of blanking periods that occur while the endoscopic system is operating.

Further, in the first embodiment, the arithmetic circuit 64 calculates the resistance value R1 of the video signal line 31 based on the predetermined voltage V1 supplied by the constant voltage circuit 23, but the method for calculating the resistance value R1 of the video signal line 31 is not limited to the above method. For example, if a cable made of the same material as the power signal line 32 is used for the video signal line 31, the resistance value R1 of the video signal line 31 can be calculated based on the diameter of the video signal line 31 and the diameter of the power signal line 32. By changing the diameter of the video signal line 31 and the diameter of the power signal line 32, the ratio R1/R2 of the resistance value R1 of the video signal line 31 to the resistance value R2 of the power signal line 32 can be controlled, and a resistance value R1 of the line 31 can be calculated. In the following, as a second embodiment, an endoscopic system in which the ratio R1/R2 of the resistance value R1 of the video signal line 31 to the resistance value R2 of the power signal line 32 is known is described.

Second Embodiment

Figure 7:
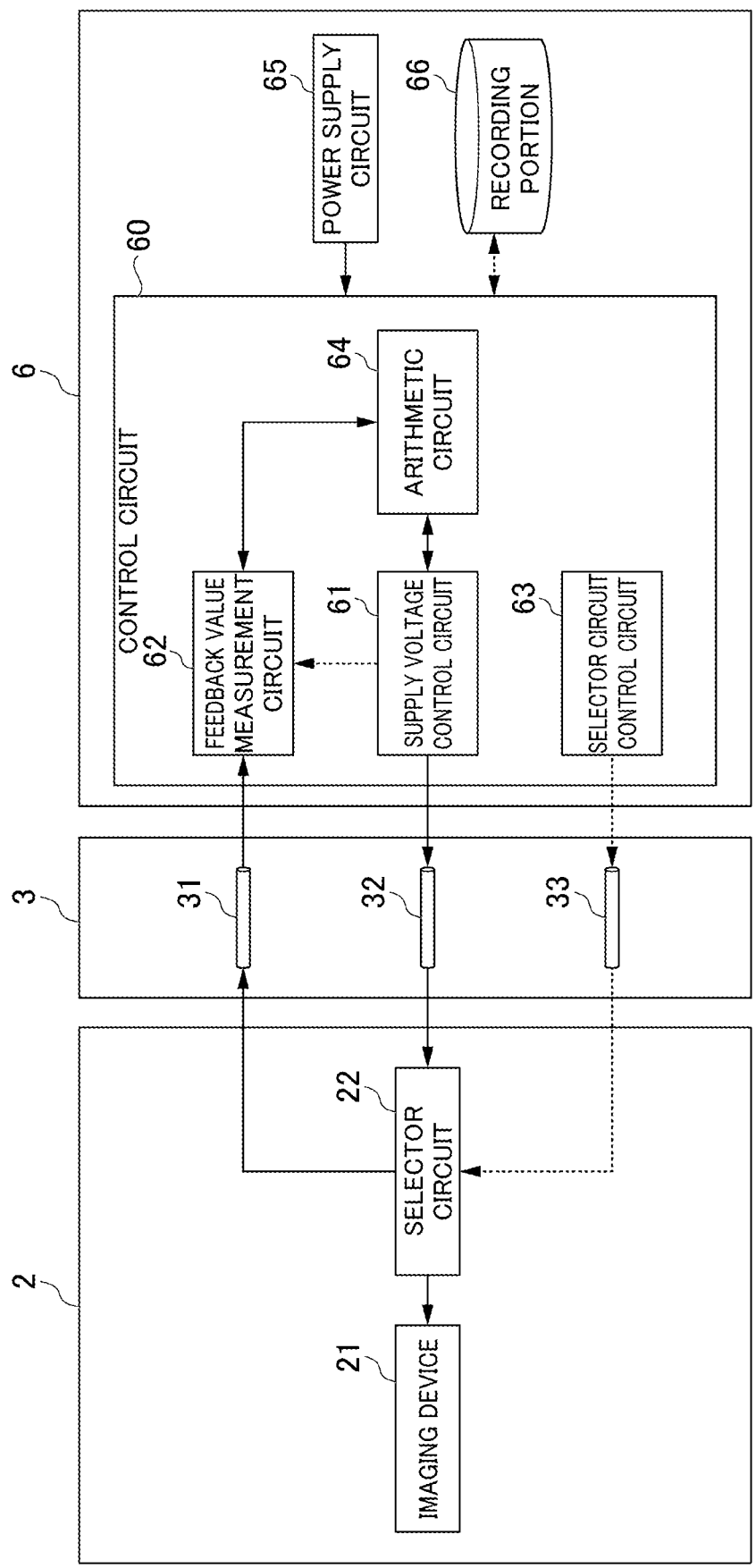
FIG. 7 is a block diagram of a camera unit and a control unit included in an endoscopic system according to a second embodiment of the present disclosure.

An endoscopic system 100B according to a second embodiment of the present disclosure will be described with reference to FIG. 7. FIG. 7 is a block diagram of the camera unit 2 and control unit 6 provided in the endoscopic system 100B according to this embodiment. In the following description, the same reference numerals are given to the same configurations as those already described, and redundant descriptions will be omitted. The endoscope system 100B differs from the endoscope system 100 of the first embodiment in that the ratio R1/R2 (=a) of the resistance value R1 of the video signal line 31 to the resistance value R2 of the power signal line 32 is already known. In the endoscopic system 100B of the present embodiment, since the ratio a of the resistance value R1 of the video signal line 31 to the resistance value R2 of the power signal line 32 is known, it is unnecessary to measure the resistance value R1 of the video signal line 31, and the constant voltage circuit 23 can be omitted.

[Operation of the Endoscopic System 100B]

Figure 8:
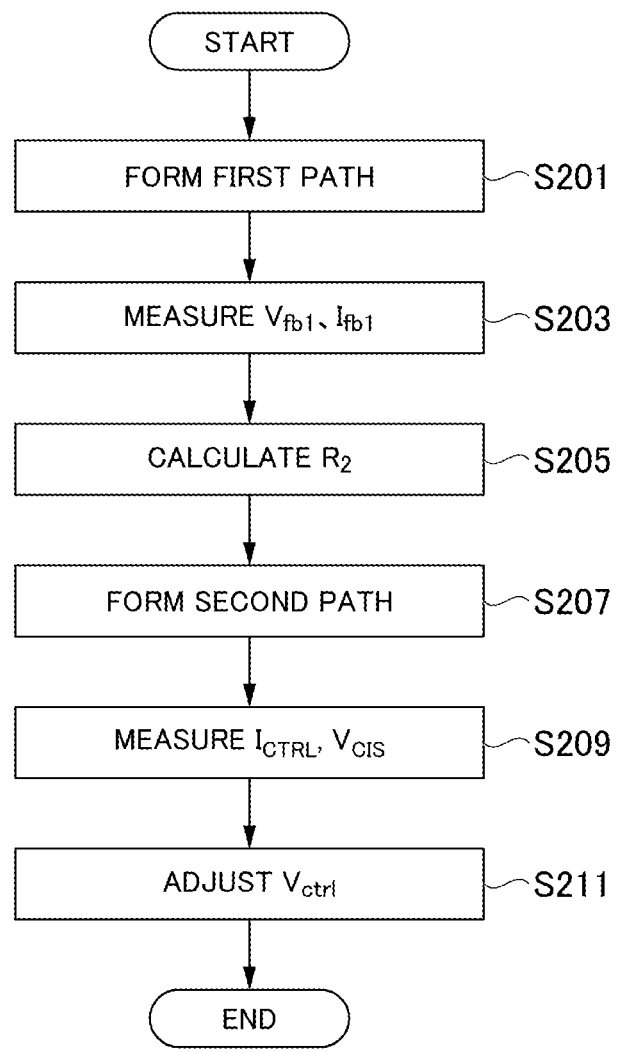
FIG. 8 is a flowchart showing an outline of operation processing executed by the endoscopic system according to the embodiment.

The operation of the endoscopic system 100B (control method of the endoscopic system 100B) will be described with reference to FIG. 8. FIG. 8 is a flowchart showing an outline of operation processing executed by the endoscopic system 100B. In the operation of the endoscopic system 100B since the ratio a of the resistance value R1 of the video signal line 31 to the resistance value R2 of the power signal line 32 is known, steps S101 to S105 in the operation of the endoscope system 100 according to the first embodiment are omitted.

In the operation of the endoscopic system 100B according to this embodiment, during the blanking period, the selector circuit control circuit 63 transmits a control signal to the selector circuit 22 via the control signal line 33, and the selector circuit 22 forms a first path to which the supply voltage control circuit 61, the power signal line 32, the video signal line 31 and the feedback value measurement circuit 62 are connected (step S201). The supply voltage control circuit 61 supplies the supply voltage Vctrl and the supply current Ictrl to the power signal line 32, and the feedback value measurement circuit 62 measures the feedback voltage Vfb1 and the feedback current Ifb1 in the first path based on the supply voltage Vctrl (step S203). The arithmetic circuit 64 calculates the sum R1+R2 of the resistance value R1 of the video signal line 31 and the resistance value R2 of the power signal line 32 from the following equation (5) (step S205). Since the ratio a of the resistance value R1 of the video signal line 31 to the resistance value R2 of the power signal line 32 is known, the following equation (5) is converted into the following equation (7), and the resistance value R2 of the power signal line 32 is calculated from the equation (7) in step S205.

$$R1+R2=(Vctrl-Vfb1)/Ifb1 \qquad \text{Expression (5)}$$

$$(1+a) \times R2=(Vctrl-Vfb1)/Ifb1 \qquad \text{Expression (7)}$$

Steps S207 to S211 in the operation of the endoscopic system 100B according to the present embodiment are the same as steps S113 to S117 in the operation of the endoscopic system 100B according to the first embodiment, so description here will be omitted.

According to the endoscopic system 100B of the present embodiment, the ratio R1/R2 of the resistance value R1 of the video signal line 31 to the resistance value R2 of the power signal line 32 is known. Therefore, compared to the operation of the endoscopic system 100, calculation of the resistance value R1 of the video signal line 31 is unnecessary. Therefore, compared to the endoscopic system 100 according to the first embodiment, the constant voltage circuit 23 becomes unnecessary. As a result, the diameter and length of the distal end portion 11 can be further reduced.

Therefore, if the ratio R1/R2 of the resistance value R1 of the video signal line 31 to the resistance value R2 of the power signal line 32 is known, the diameter of the video signal line 31 and the diameter of the power signal line 32 may be different from each other, or the diameter of the video signal line 31 and the diameter of the power signal line 32 may be substantially the same.

The program in each embodiment may be recorded in a computer-readable recording medium, and the program recorded in this recording medium may be read into a computer system and executed. The "computer system" includes hardware such as an OS and peripheral devices. The term "computer-readable recording medium" refers to portable media such as flexible discs, magneto-optical discs, ROMs and CD-ROMs, and storage devices such as hard discs incorporated in computer systems. Furthermore, the "computer-readable recording medium" may include those that dynamically retain the program for a short period of time like a communication line for transmitting a program via a network such as the Internet or a communication line such as a telephone line, and those that retain the program for a certain period of time like the volatile memory inside the computer system that becomes the server and client in that case. Further, the program may be for realizing some of the functions described above, or may be capable of realizing the functions described above in combination with a program already recorded in the computer system.

What is claimed is:

1. An imaging system in which a camera unit and a control unit are connected by a transmission cable having a power signal line and a video signal line,
wherein the camera unit comprises
an imaging device that is driven by a drive voltage Vcis and generates a photoelectric conversion signal according to the amount of light received, and
a selector circuit that switches a current flow path so that a resistance value R2 of the power signal line can be calculated, and
the control unit comprises
a supply voltage control circuit that controls a supply voltage Vctrl,
a feedback value measurement circuit that measures a feedback voltage Vfb that is a voltage on the control unit side of the video signal line, a feedback current Ifb that is a current on the control unit side after passing through the video signal line, and a supply current Ictrl corresponding to the supply voltage Vctrl, and
an arithmetic circuit that calculates a resistance value R3 related to a resistance value R1 of the video signal line and a resistance value R2 of the power signal line from the supply voltage Vctrl, the feedback voltage Vfb and the feedback current Ifb, and calculates a drive voltage Vcis based on the resistance value R2, the supply current Ictrl, and the supply voltage Vctrl.

2. The imaging system according to claim 1, wherein the arithmetic circuit transmits a calculation result of the drive voltage Vcis to the supply voltage control circuit, and the supply voltage control circuit adjusts the supply voltage Vctrl based on the calculation result.

3. The imaging system according to claim 1, wherein the selector circuit switches the path between a first path formed by connecting the supply voltage control circuit, the power signal line, the video signal line, and the feedback value measurement circuit, and a second path formed by connecting the supply voltage control circuit, the power signal line, and the imaging device.

4. The imaging system according to claim 1, wherein
the camera unit further comprises a constant voltage circuit that supplies a constant voltage V1, and
the arithmetic circuit calculates the resistance value R1 of the video signal line from the constant voltage V1, the voltage Vfb, and the current Ifb based on the following equation (3), $$R1=(V1-Vfb)/Ifb \quad \text{Equation (3)}.$$

5. The imaging system of claim 4, wherein the selector circuit switches the path between a third path formed by connecting the supply voltage control circuit, the power signal line, the constant voltage circuit, the video signal line, and the feedback value measurement circuit, a first path formed by connecting the supply voltage control circuit, the power signal line, the video signal line, and the feedback value measurement circuit, and a second path formed by connecting the supply voltage control circuit, the power signal line, and the imaging device.

6. The imaging system according to claim 1, wherein the ratio R1/R2 of the resistance value R1 of the video signal line to the resistance value R2 of the power signal line is known.

7. The imaging system according to claim 1, wherein the power signal line and the video signal line have substantially the same diameter.

8. The imaging system according to claim 1, wherein the arithmetic circuit calculates the resistance value R1 of the power signal line during a blanking period.

9. A control unit that is connectable to a camera unit equipped with an imaging device via a power signal line and a video signal line, comprising:
a supply voltage control circuit that controls the supply voltage Vctrl;
a feedback value measurement circuit that measures a feedback voltage Vfb that is a voltage on the control unit side of the video signal line, a feedback current Ifb that is a current on the control unit side after passing through the video signal line, and a supply current Ictrl corresponding to the supply voltage Vctrl; and
an arithmetic circuit that calculates a resistance value R3 related to a resistance value R1 of the video signal line and a resistance value R2 of the power signal line from the supply voltage Vctrl, the feedback voltage Vfb, and the feedback current Ifb, and calculates a drive voltage Vcis from the resistance value R2, the supply current Ictrl, and the supply voltage Vctrl.

10. An endoscopic system comprising the imaging system according to claim 1.

* * * * *